(12) United States Patent
Jiang et al.

(10) Patent No.: US 9,169,961 B1
(45) Date of Patent: Oct. 27, 2015

(54) LIFTING APPARATUS FOR GASLESS LAPAROSCOPIC SURGERY

(76) Inventors: Jeng-Kai Jiang, Taipei (TW); Shyh-Jen Wang, Taipei (TW)

( * ) Notice: Subject to any disclaimer, the term of this patent is extended or adjusted under 35 U.S.C. 154(b) by 682 days.

(21) Appl. No.: 12/929,419

(22) Filed: Jan. 24, 2011

(51) Int. Cl.
  F16M 11/00 (2006.01)
  F16M 11/12 (2006.01)
  F16M 13/02 (2006.01)

(52) U.S. Cl.
  CPC .............. *F16M 11/12* (2013.01); *F16M 13/02* (2013.01)

(58) Field of Classification Search
  CPC ........ F16M 13/02; F16M 11/12; F16M 11/04
  USPC ............. 248/124.1, 124.2, 125.8, 125.2, 127,
    248/158, 223.41, 230.1, 230.2, 519, 539,
    248/541, 540, 292.12, 222.13, 222.14, 74.5,
    248/201, 412, 413, 276.1, 278.1, 295.11,
    248/285.1; 403/97, 105, 104, 398, 343;
    600/27, 229, 227, 231, 204; 128/96.1,
    128/845, 200.11–200.13, 207.29; 74/415
  See application file for complete search history.

(56) References Cited

U.S. PATENT DOCUMENTS

| | | | |
|---|---|---|---|
| 1,149,762 A * | 8/1915 | Hendrickson | 248/295.11 |
| 1,902,401 A * | 3/1933 | Gunning | 254/95 |
| 2,985,415 A * | 5/1961 | Stahl | 248/125.2 |
| 5,020,195 A * | 6/1991 | LeVahn | 24/514 |
| 5,372,147 A | 12/1994 | Lathrop, Jr. et al. | |
| 5,400,772 A * | 3/1995 | LeVahn et al. | 600/230 |
| 5,501,653 A | 3/1996 | Chin | |
| 5,505,689 A | 4/1996 | Kramer et al. | |
| 5,555,897 A | 9/1996 | Lathrop, Jr. et al. | |
| 5,569,165 A | 10/1996 | Chin et al. | |
| 5,690,607 A | 11/1997 | Chin et al. | |
| 5,704,900 A | 1/1998 | Dobrovolny et al. | |
| 5,716,327 A | 2/1998 | Warner et al. | |
| 5,813,647 A * | 9/1998 | Chen | 248/354.7 |
| 5,823,946 A | 10/1998 | Chin | |
| 6,023,989 A * | 2/2000 | Imase et al. | 74/422 |
| 6,315,718 B1 * | 11/2001 | Sharratt | 600/228 |
| 6,618,878 B1 | 9/2003 | McCoy, Jr. et al. | |
| 6,676,328 B2 | 1/2004 | Wang et al. | |
| 2002/0131818 A1 * | 9/2002 | Wang et al. | 403/290 |
| 2005/0113645 A1 * | 5/2005 | Sharratt et al. | 600/227 |

FOREIGN PATENT DOCUMENTS

| | | | | |
|---|---|---|---|---|
| KR | 100945193 B1 * | 3/2010 | | F16H 1/24 |

* cited by examiner

*Primary Examiner* — Kimberly Wood

(57) ABSTRACT

A lifting apparatus of surgery comprises a vertical post, a horizontal arm, a rack slider and a vertical rack. One end of vertical post is mounted on a surgical table; and the other end is to be slid on and pivoted by the horizontal arm. The horizontal arm includes a hole to slide and pivot on vertical post, a shaft to be slid on by rack slider and a fastening means to secure horizontal arm on vertical post. The rack slider includes a hole to slide on a shaft of horizontal arm, and a lifting mechanism to engage with vertical rack. The vertical rack includes a rack to engage with lifting mechanism of rack slider and an adaptor to couple with a distension instrument. First clamp vertical post on a surgical table. Then slide and secure horizontal arm on vertical post to desired position. Following slide rack slider on horizontal arm to desired position such as above patient's abdominal wall. Then, engage rack slider with vertical rack to provide upward lifting by turning the handle of lifting mechanism on rack slider.

10 Claims, 6 Drawing Sheets

LIFTING APPARATUS FOR GASLESS LAPAROSCOPIC SURGERY

TECHNICAL FIELD

The present invention relates generally to the structure and use of surgical instruments and, more particularly, to positionable support structures for manipulating parts of the body in gasless laparoscopic surgical procedures.

BACKGROUND OF THE INVENTION

Laparoscopic surgery is generally performed through small incisions in the abdomen using specialized instruments to accomplish the desired surgical procedures. Usually, the instruments are introduced through a narrow diameter tube, such as a trocar sleeve, while the physician observes manipulation of the instruments through specialized imaging equipment, such as a laparoscope. Laparoscopic surgical techniques offer significant advantages over conventional "open" surgical procedures, including better cosmetics effect, less postoperative pain, decrease resumption of gastrointestinal function and early return to work.

In laparoscopic surgical procedures, it is generally necessary to lift the abdominal wall away from the underlying abdominal organs to improve the visibility and accessibility of such organs. Such distension of the abdominal cavity, or peritoneum, has been heretofore accomplished by injecting a gas such as $CO_2$ into the peritoneal cavity to tent-up the interior of the abdominal wall. The insufflation thus requires gas seals to be present at all entry ports through the abdominal wall; and, because of the doming effect on the abdomen, the laparoscopic instruments (graspers, scissors, electrocautery instruments, etc.) need long shafts to reach the treatment site. Further, using the insufflation technique, maintenance of the required distension is complicated by the loss of gas through the entry ports through the abdominal wall.

It has been proposed to use mechanical systems for peritoneal distension to overcome the problems associated with the insufflation technique. For example, U.S. Pat. No. 538,012 and Hashimoto et al. (Laparoscopic cholecystectomy: an approach without pneumoperitoneum, Surgical Endoscopy, 1994, pp. 54-56) adopts an alternative to abdominal insufflation, by upward and outward traction on the anterior abdominal wall with a hanger lifting method using subcutaneous wiring. However, the wires hung above the abdominal wall may obstruct the operators' actions during operation.

Chin et al. disclose the Laparofan® technique for lifting the abdominal wall by means of angle-shaped rods having elongated arms at their distal ends which are inserted through an incision and farmed out within the abdomen. (Gasless laparoscopy using a planar lifting technique, Journal of American College of Surgery, 1993, Vol. 178, pp 401-403) Most of Chin et al.'s patents mainly focus on the fan retractors. For example, U.S. Pat. No. 5,501,653 utilizes a pair of lifting rods each hinged at their distal ends to opposite ends of an elongate cross-member. After insertion, the apparatus is locked into the triangular configuration, connected to a lifting arm, and lifted to cause the retraction rods to lift and support the abdominal wall.

U.S. Pat. No. 5,505,689 discloses a fan retractor for laparoscopic surgery which has a pair of angle-shaped elements with first legs disposed in parallel relationship to one another and second legs extending laterally from the first legs for movement between a juxtaposed collapsed condition and a fanned-out expanded condition.

U.S. Pat. Nos. 5,569,165 and 5,690,607 provide an apparatus for allowing two fan retractors to be used to lift the abdominal wall and to provide improved visualization and working space in the abdomen of obese patients, and in the lateral regions of the abdomen of normal patients.

Similarly, U.S. Pat. No. 5,716,327 utilizes a lifting body having two or more retraction rods supported by the lifting body. The retraction rods are spread apart from each other while their parallel orientation is maintained. The lifting body is connected to a lifting arm and lifted, causing the retraction rods to lift and support the abdominal wall.

U.S. Pat. No. 5,823,946 discloses a mechanical lifting retractor to increase working space in the chest for cardiac surgery by temporarily expanding the space between the rib cage and the pericardium. The lifting device has a pair of parallel right-angled retractors. Following insertion of the distal portions into the mediastinal space, the distal portions are rotated into the lifting position and oriented in the sagittal plane such that each distal portion extends beneath one of the ribs. A lifting force is applied to the lifting retractor, causing the distal portions to engage the ribs and to lift the rib cage and thereby enlarging the mediastinal space.

All of these retractors or apparatus mentioned above require a mechanical lifting arm to provide the lifting force. However, none of these patents mentioned above fully disclosed the arm.

Chin et al.'s U.S. Pat. Nos. 5,372,147 and 5,555,897 do describe a mechanical lifting arm. The arm comprises a support structure including an extendible vertical post, an extendible horizontal arm, and means at the lower end of the post for mounting the structure to a surgical table. A mechanism is provided for releasably locking the position of the horizontal arm relative to the vertical post including an actuator switch at the distal end of the horizontal arm. Furthermore, the arm is provided for power-assisted raising and lowering of the vertical post. Although power assisted raising of the arm provides quick and controlled lifting of the body structure, the power requirement also made the system to be kind of complicated.

Furthermore, U.S. Pat. No. 5,704,900 also discloses an apparatus for peritonal distension with manual operation. The apparatus is a surgical instrument support structure including a substantially vertical post having a gear rack disposed generally along the post's axis and an arm assembly movably coupled along the gear rack extending from the gear rack for holding a surgical instrument. The arm assembly includes a circular gear rotatably coupled to the arm assembly in engagement with the gear rack and a mechanism for rotating the circular gear, whereby rotation of the circular gear raises and lowers the arm assembly relative to the vertical post. The '900 apparatus using the circular gear to raise and lower the whole arm including the distension instrument may also increase the possibility of structure instability. The apparatus is not only complicate but also has a support, elbow and distal end to increase the instability problem.

For these reasons, it would be desirable to provide improved apparatus for lifting the distension instrument, particularly for providing a stable lifting force during gasless laparoscopic surgical procedures. In particular, the apparatus should provide for lifting of the abdominal wall or other body structure without using power-assisted lifting and lowering. The apparatus should allow easily manual manipulation and stable support the lifting.

SUMMARY OF THE INVENTION

The object of this invention is to provide an apparatus for lifting the distension instrument, particularly for providing the lifting force during gasless laparoscopic surgical procedures. It is also another object of the present invention to provide a positionable support structure for lifting the abdominal wall or other body structure. Another object of this invention is to provide height and horizontal position adjustment to set the apparatus in the desire position. Also another object of the invention is to offer a vertical rack for manually adjusting the height of the lifting. Still another object of this present invention is to adopt various fastening means for fastening a part on a rod or column securely.

According to the present invention, an improved apparatus is provided for lifting the distension instrument, particularly for providing the lifting force during gasless laparoscopic surgical procedures. The apparatus comprises a support structure including a vertical post, a horizontal arm, a rack slider and a vertical rack. One end of the post is utilized a clamp to mount the whole structure on a surgical table. One end of the horizontal arm has a hole to slide along the other end of the post and a fastening device to fasten the horizontal arm on the vertical post. The rack slider has a hole to slide along the other end of the horizontal arm and a rack hole to engage with the vertical rack. The vertical rack engages with the rack slider and has an adaptor on the other end to match with the fan retractor.

Thus, the surgeon can use a clamp to mount the vertical post on a surgical table, adjust the horizon arm to a proper height and orientation. Then fasten the horizon arm on the vertical post. Following, slide and fasten the rack slider on the proper position along the horizon arm. In this way, after the rack slider has been properly positioned, the vertical rack can be raised to perform a desired physical distension or other manipulation. Preferably, the raising and lowering of the vertical rack is adjusted by the surgeon with a handle on the rack slider.

BRIEF DESCRIPTION OF THE DRAWINGS

FIG. 5C(b) is an exploded detailed view of the third type of fastening means of the horizontal arm of FIG. 2 and f the rack slider of FIG. 3.

FIG. 5D(b) is an exploded detailed view of the fourth type of fastening means of the horizontal arm of FIG. 2 and f the rack slider of FIG. 3.

DETAILED DESCRIPTION OF THE ILLUSTRATIVE EMBODIMENTS

In the exemplary apparatus of the present invention, the vertical post is mounted on a surgical table; the horizontal arm is positioned over a patient on the table; the rack slider is fastened on the horizontal arm and the rack is engaged on the rack slider. Surgical instruments adapted for coupling to the abdominal cavity or other body structures are then attached to the distal end of the rack and the rack is raised, usually by turning the handle on the rack slider, lifting the abdominal wall or other body structures of the patient.

The positionable support structure is easily manipulated by the user by sliding the horizontal arm and rack slider, and then fastening them to the desired location. Manual raising of the rack provides stable and controlled lifting of the body structure. Moreover, in laparoscopic surgery, the use of such a positionable support structure eliminates the need for gas insufflation, and the associated problems of gas loss through entry ports to the abdominal cavity and doming of the abdomen. Further, the degree of distension can be manually manipulated to minimize traumatic impact on the patient.

In a preferred aspect of the present invention, the positionable support structure includes a hole and a fastening means in both the horizontal arm and rack slider. The holes of the horizontal arm and rack slider allow them to slide on the vertical post and horizontal arm, respectively, to the intended position. The fastening means can be a bolt to directly press the rod, a bolt to clamp the rod, the fastening means described in U.S. Pat. No. 6,618,878 or the simplified fastening means described in U.S. Pat. No. 6,676,328.

This apparatus will usually be mountable to a surgical table, preferably to the mounting rail which is of a standard size and shape for a variety of surgical tables. One end of the vertical post of this invention is mounted with a surgical table clamp which allows the whole apparatus to be rigidly clamped in position at a desired point along the rail. Preferably the clamp can be quickly applied and released to allow the support structure to be moved along the rail or removed altogether with little time or effort required. The table clamp is available in the market or for example as described in U.S. Pat. Nos. 4,796,836, 4,971,037, 5,152,486, 6,622,980 or 7,857,271.

Figure 1:
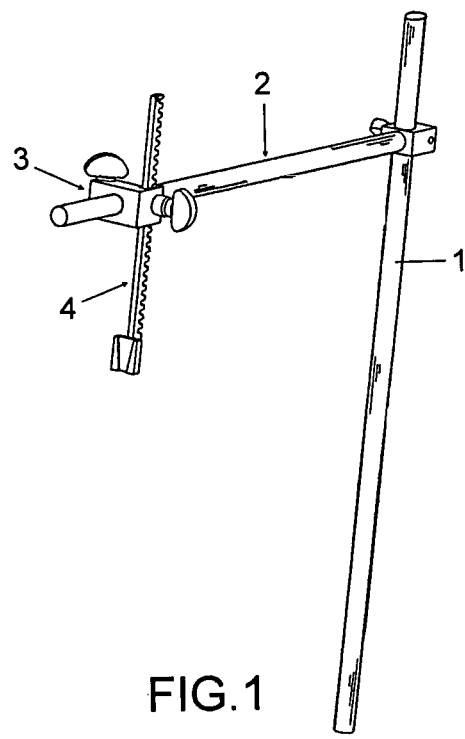
FIG. 1 is a perspective view of a positionable support structure constructed according to the principles of the present invention.

Referring now to FIG. 1, an embodiment of the present invention comprises a vertical post 1, a horizontal arm 2, a rack slider 3, a vertical rack 4. One end of the vertical post 1 is mounted on a surgical table (not shown). The other end of the vertical post 1 is allowed the horizontal arm 2 to slide on and adjust the height and orientation of the horizontal arm relative to the surgical table.

Figure 2:
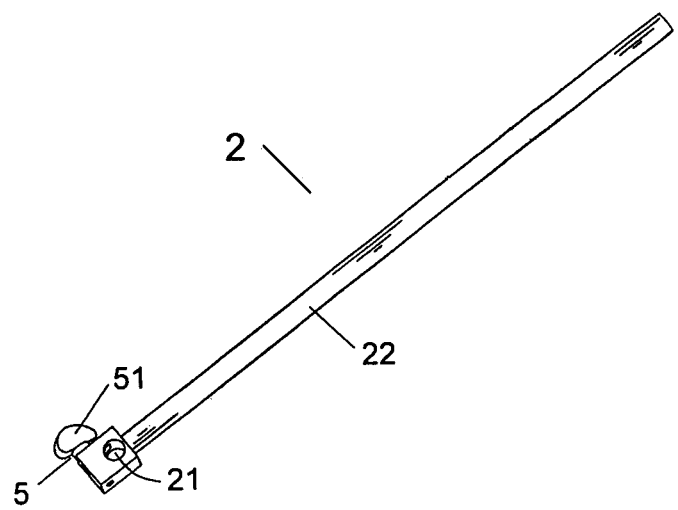
FIG. 2 is a perspective view of the horizontal arm of the structure of FIG. 1.

As shown in FIG. 2, the horizontal arm 2 includes a hole 21, a shaft 22 and a fastening means 5. The hole 21 of the horizontal arm 2 is allowed the arm to slide and pivot on the vertical post 1 to adjust the height and orientation of the arm relative to the surgical table. After setting the height and orientation, a user can turn the fasten handle 51 to drive the fastening means 5 to fasten the horizontal arm 2 on the vertical post 1.

Figure 3:
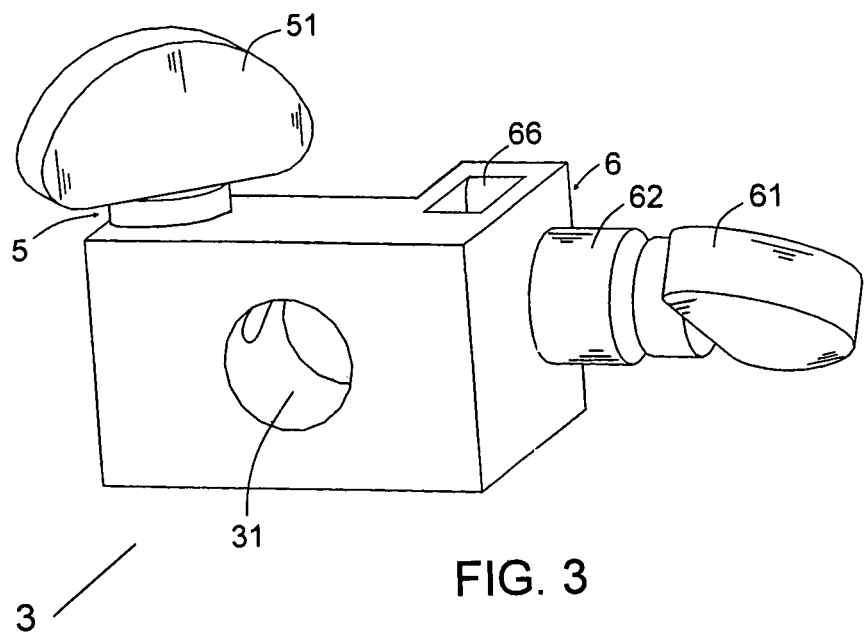
FIG. 3 is a perspective view of the rack slider of the structure of FIG. 1.

Referring now to FIG. 3, a rack slider 3 includes a hole 31, a fastening means 5 and a lifting mechanism 6. The rack slider 3 can slide on the shaft 22 of the horizontal arm 2 through the hole 31. Following, the fastening means 5 can lock the rack slider 3 on the position desired. The lifting mechanism 6 is engaged with the vertical rack 4 in the rack slot 66 to provide the lifting force by turning the handle 61 to rotate a pivot 62.

Figure 4:
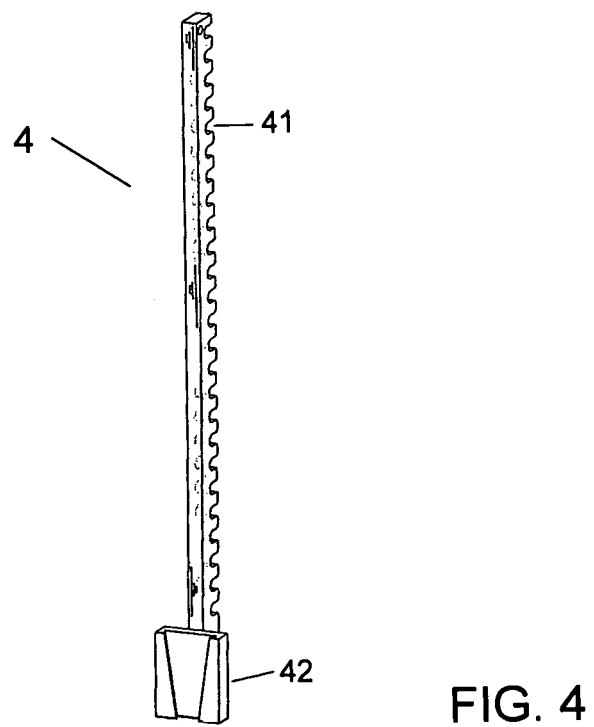
FIG. 4 is a perspective view of the vertical rack of the structure of FIG. 1.

As shown in FIG. 4, the vertical rack 4 includes a rack 41 and an adaptor 42. The rack 41 can engaged with the lifting mechanism 6 of rack slider 3 to provide the lifting. The adaptor 42 is on the other end of the vertical rack 4 to engage with the Laparofan® or other abdominal distension instrument (not shown). The adaptor 42 can be in the format of dovetail (as shown in FIG. 4), pin, bolt or hook connector (not shown).

Figure 5A:
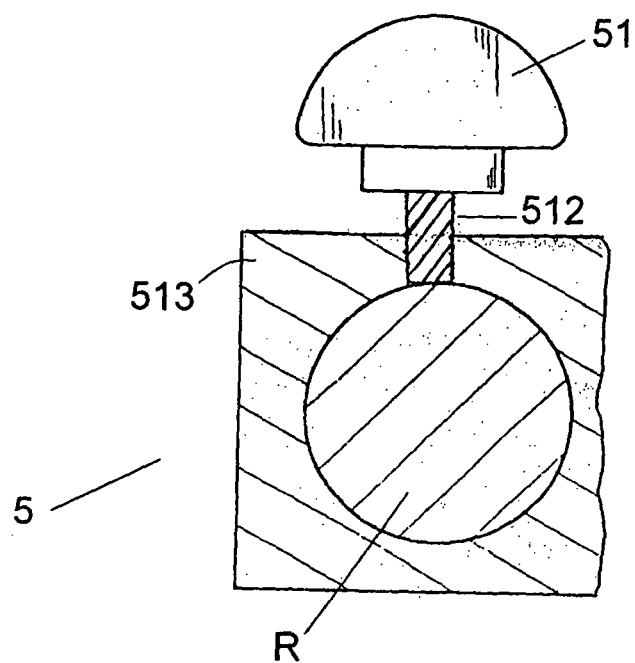
FIG. 5A is the cross-sectional view of the first type of fastening means of the horizontal arm of FIG. 2 and f the rack slider of FIG. 3.
Figure 5B:
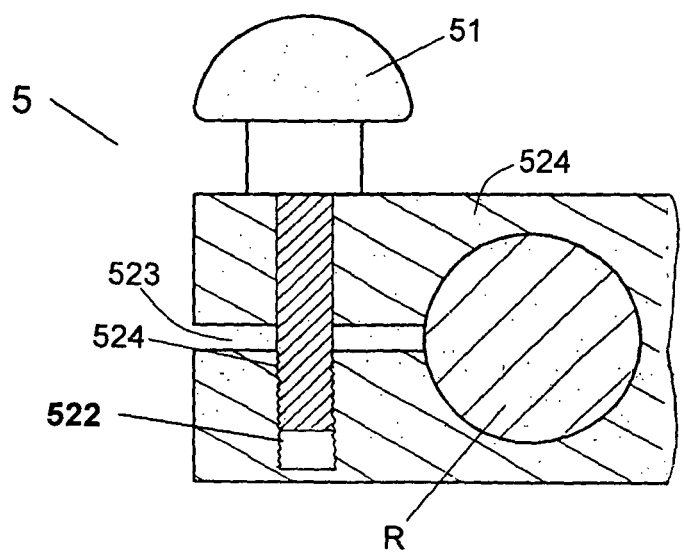
FIG. 5B is the cross-sectional view of the second type of fastening means of the horizontal arm of FIG. 2 and f the rack slider of FIG. 3.

The fastening means 5 of horizontal arm 2 or a rack slider 3 can be a bolt to directly press the rod, a bolt to clamp the rod, the fastening means described in U.S. Pat. No. 6,618,878 or the simplified fastening means described in U.S. Pat. No. 6,676,328. As shown in FIG. 5A, the handle 51 of the fastening means 5 has a screw portion 512 to engage with the base 513 to compress the rod R. The second fastening means demonstrated in FIG. 5B has a screw portion 522 and gap 523 in the base 524. Drive the handle 51 can deform the gap 523 to clamp the rod R.

Figure 5C:
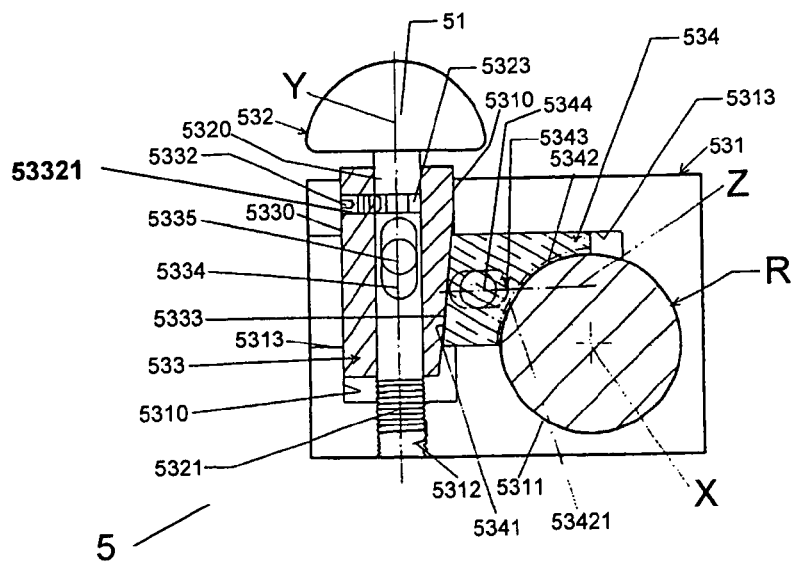
FIG. 5C(a) is the cross-sectional view of the third type of fastening means of the horizontal arm of FIG. 2 and f the rack slider of FIG. 3.
Figure 5C:
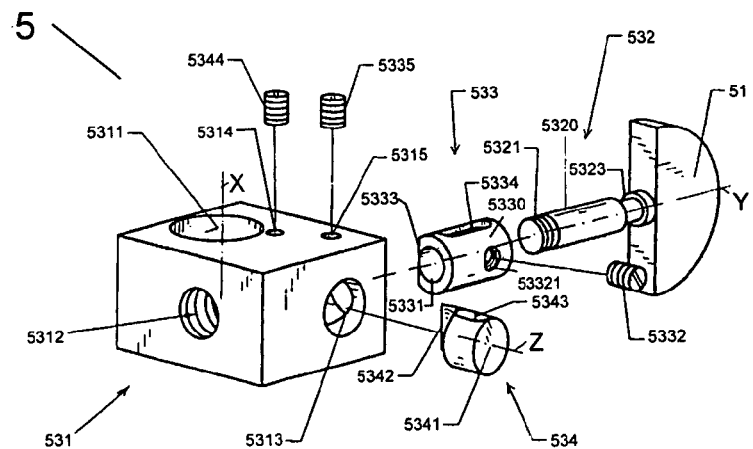

The third fastening means 5 shown in FIG. 5C(a) and FIG. 5C(b) has disclosed in U.S. Pat. No. 6,619,878. The fastening means 5 comprises: a holding base 531 capable of sliding or rotating on a rod or rod-like fixture R; a driving bolt 532 rotatably engageable with the holding base 531; a thrusting block 533 rotatably coupled with the driving bolt 532 and reciprocatively held in the holding base 531; and a follower block 534 tangentially engageable with the thrusting block 533 and reciprocatively moving in the holding base 531; whereby upon rotating the driving bolt 532, the thrusting block 533 forwarding simultaneously to thrust the follower block 534, then to interfere in the surface of the rod R for firmly fastening the rod R in (or with) the holding base 531. The holding base 531 may be integrally formed with or detachably mounted on a fixed object, a fixture, a platform or a building structure (not shown). The rod R may be positioned vertically, horizontally or at any angles to be fastened with the fastening means of the present invention. The fastening means may be made of metals, engineering plastics, composites, or any other suitable materials. The holding base 531 includes: a rod hole 5311 longitudinally formed in or through the holding base capable of sliding or rotating with the rod R about a longitudinal axis X; a first block hole 5310 transversely formed in the holding base 531 about a first latitudinal axis Y projectively perpendicular to the longitudinal axis X; a screw hole 5312 formed in the holding base 1 and coaxially communicated with the first block hole 5310 about the first latitudinal axis Y; and a second block hole 5313 transversely formed in the holding base 531 about a second latitudinal axis Z perpendicular to the first latitudinal axis Y to be perpendicularly intersected with the first block hole 5310. The driving bolt 532 includes: a bolt shank portion 5320, a screw portion 5321 having male threads formed thereon and formed on a distal end of the shank portion 5320 to be engageable with the screw hole 5312 formed in the holding base 531, a handle (or knob) 51 formed on a proximal end of the shank portion 5320, and a neck portion 5323 annularly recessed in the shank portion 5320 adjacent to the handle portion 51. The thrusting block 533 includes: a sleeve member 5330 capable of sliding in the first block hole 5310 formed in the holding base 531, a bolt hole 5331 longitudinally formed through the sleeve member 5330 and rotatably engageable with the shank portion 5320 of the driving bolt 532, a screw 5332 rotatably formed in a screw hole 53321 transversely formed through the sleeve member 5330 and engageable with the neck portion 5323 of the driving bolt 532 for rotatably coupling the driving bolt 532 with the thrusting block 533, a driving wedge face 5333 formed on a side surface of the sleeve member 5330 and tapered inwardly towards the first latitudinal axis Y, a first elongate slot 5334 formed in the sleeve member 5330 parallel to the first latitudinal axis Y, and a first limiting screw 5335 secured in the holding base 531 through a screw hole 5315 and slidably engageable with the first elongate slot 5334 for preventing an axial rotation of the sleeve member 5330 about the first latitudinal axis Y. The follower block 534 includes: a follower wedge face 5341 formed on a first end portion of the follower block 534 to be tangentially engageable with the driving wedge face 5333 of the thrusting block 533, a recess portion 5342 recessed in a second end portion of the follower block 534 opposite to the follower wedge face 5341 in order to interfere in (or to interferentially hold) the rod R, a second elongate slot 5343 formed in the follower block 4 parallel to the second latitudinal axis Z, and a second limiting screw 5344 secured in the holding base 1 through a screw hole 5314 and slidably engageable with the second elongate slot 5343 for preventing an axial rotation of the follower block 534 about the second latitudinal axis Z. The recess portion 5342 may be formed as an arcuate shape in order to be well engaged with a cylindrical surface of the rod R if formed as a cylindrical shape. A packing layer 53421, which is made of rubber or elastomer materials, may be formed on the recess portion 42 to increase its frictional contact with the rod surface. When fastening the rod R with the fastening means 5 by passing the rod R in the rod hole 5311 of the holding base 531, the driving bolt 532 is rotated (for example in a clockwise direction) about the axis Y to protrude inwardly in the block hole 5310 and screw hole 5312 to simultaneously move the thrusting block 533 inwardly, whereby the follower wedge face 5341 of the follower block 534 will be thrusted by the driving wedge face 5333 of the thrusting block 533 to push the follower block 534 towards the rod R, then the recess portion 5342 of the follower block 534 is interfered in the rod surface of the rod R, thereby firmly fastening the rod R within the holding base 531. For loosening or separating the rod from the base 531, the driving bolt 532 is rotated in a reverse direction to loose the block 534 from the rod.

Figure 5D:
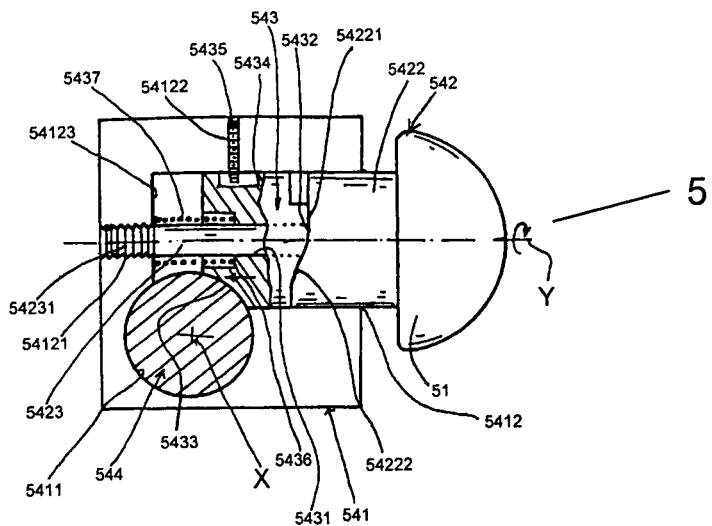
FIG. 5D(a) is the cross-sectional view of the fourth type of fastening means of the horizontal arm of FIG. 2 and f the rack slider of FIG. 3.
Figure 5D:
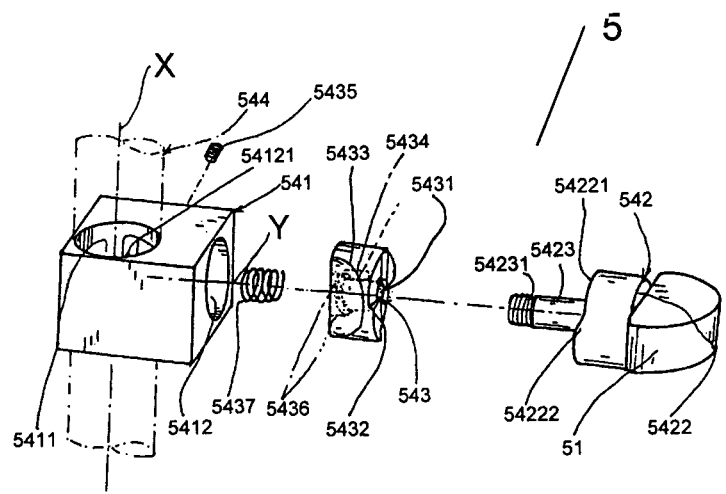

The forth fastening means shown in FIG. 5D(a) and FIG. 5D(b) has disclosed in U.S. Pat. No. 6,676,328. The fastening means 5 comprises: a holding base 541 slidably engageable with a rod (or column) 544; a thrusting bolt 542 rotatably secured in the holding base 541; and a pressing block 543 reciprocatively moving in the holding base 541 and operatively propelled by the thrusting bolt 542 to interfere in and firmly fasten the rod 544 on the holding base 541. The holding base 541 includes: a rod hole 5411 longitudinally formed in the holding base 541 defining a longitudinal axis X at the center of the rod hole 5411 and slidably or rotatably engageable with the rod 544, a cam hole 5412 transversely formed in the holding base 541 about a latitudinal axis Y defined at a center of the cam hole 5412 and projectively perpendicular to the longitudinal axis X, and a bolt hole 54121 formed in the holding base 541 having a diameter smaller than that of the cam hole 5412 and coaxially communicated with the cam hole 5412 about the latitudinal axis Y. The thrusting bolt 542 includes: a handle (or knob) 51, a cylindrical shank portion 5422 connected with the handle 51 and rotatably engageable with the cam hole 5412 in the holding base 541, a cam portion 54221 formed on an inner end portion of the shank portion 5422 having at least a thrusting sloping portion 54222 concentrically formed on the cam portion 54221 for operatively engaging and propelling the pressing block 543 inwardly for fastening the rod 544 between the holding base 541 and the pressing block 543 of the fastening means of the present invention, and a screw portion 5423 having male threads 54231 formed on the screw portion 5423 and engaging with the bolt hole 54121 formed in the holding base 541, with the screw portion 5423 protruding inwardly from the shank portion 5422 to pass through the pressing block 543 to be engaged with the bolt hole 54121 in the holding base 541. The pressing block 543 includes: a central hole 5431 formed through the pressing block 543 for passing the screw portion 5423 of the thrusting bolt 542 through the central hole 5431, at least a follower sloping portion 5432 concentrically formed on an outer end portion of the pressing block 543 to be tangentially engaged with and inwardly propelled by the thrusting sloping portion 54222 formed on the thrusting bolt 542, a recess portion 5433 arcuately recessed in an inner end portion of the pressing block 543 opposite to the follower sloping portion 5432 and engageable with the cylindrical (arcuate) surface of the rod 543 in order to interfere in and to firmly fasten the rod 544, a groove 5434 longitudinally recessed in a side portion of the pressing block 543 and slidably engaging with a guiding screw 5435 inserted through a screw hole 54122 in the holding base 541 for longitudinally guiding a reciprocal movement of the pressing block 543 in the cam hole 5412 when driven or actuated by the thrusting bolt 542, and a socket 5436 recessed in an inner central portion of the pressing block 543 to be coaxially aligned with the central hole 5431 of the pressing block 543 for retaining a restoring spring 5437 in between the socket 5436 and a seat portion 54123 formed in the holding base 544 adjacent to the screw hole 54121 for tensioning the pressing block 543 to be resiliently coupled with the thrusting bolt 542. When fastening the rod 544 by the present invention, the handle 51 of the thrusting bolt 542 is rotated about the axis Y to engage the thrusting sloping portion 54222 of the bolt 542 with the follower sloping, portion 5432 of the pressing block 543 to propel the pressing block 543 inwardly to allow the recess portion 5433 of the block 543 to interfere in the rod 544 for firmly fastening the rod 544 in between the block 543 and the holding base 541 of the present invention. The screw 5435 serves to guide an axial forward moving of the block 543 as driven by the bolt 542. The spring 5437 forces the block 543 coupling with the bolt 542, so that the follower sloping portion 5432 of the block 543 can engage with the thrusting sloping portion 54222 of the bolt 542 for accelerating the fastening operation. Upon a reverse rotation of the handle 51 to uncouple the thrusting portion 54222 of the bolt 542 from the follower portion 5432 of the block 543, the restoring spring 5437 will force the block 543 to disengage from the rod 544 and then to release from the rod 544. With the restoring spring 5437 forcing the block 543 towards the bolt 542, the fastening means of the present invention certainly can disengage from the rod 544 very quickly. With engagement of the screw portion 54231 in the bolt hole 54121 in an axial direction (Y), the block 543 can not be rotated but transversely moved as limited by the screw 5435 in the longitudinal groove 5434, while the spring 5437 forces the block 543 to be engaged with the bolt 542 so that the steps prevent the bolt 542 from being rotated in opposite direction, thereby preventing the bolt 542 from being loosened or released from the holding base 541.

Figure 6:
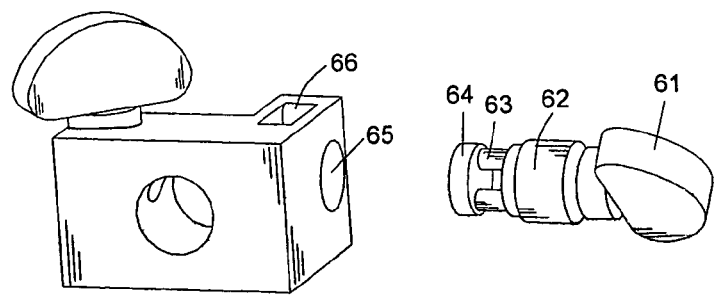
FIG. 6 is an exploded detailed view of the lifting mechanism of the rack slider of FIG. 3.

Referring to FIG. 6, the lifting mechanism 6 includes a handle 61, a pivot 62, two extending pins 63, a disc 64, a pinion hole 65 and a rack slot 66. The handle 61 is mounted on one end of the pivot 62 so that the pivot 62 can be rotated by the handle 61. On the other end of the pivot 62, two extending pins 63, spaced at a proper distance, are attached to the disc 64 so that these two extending pins 63 can engage with the vertical rack. As the handle 61 is rotated, the extending pins 63 engage the teeth 41 of the vertical rack 4 in the rack slot 66 to form a rack and pinion system in the pinion hole 65. The lifting force can be provided by turning the handle 61 to make the vertical rack 4 upward. When the pivot 62 is in the proper position, the lifting mechanism 6 is locked to resist the forces which would tend to downward.

Figure 7:
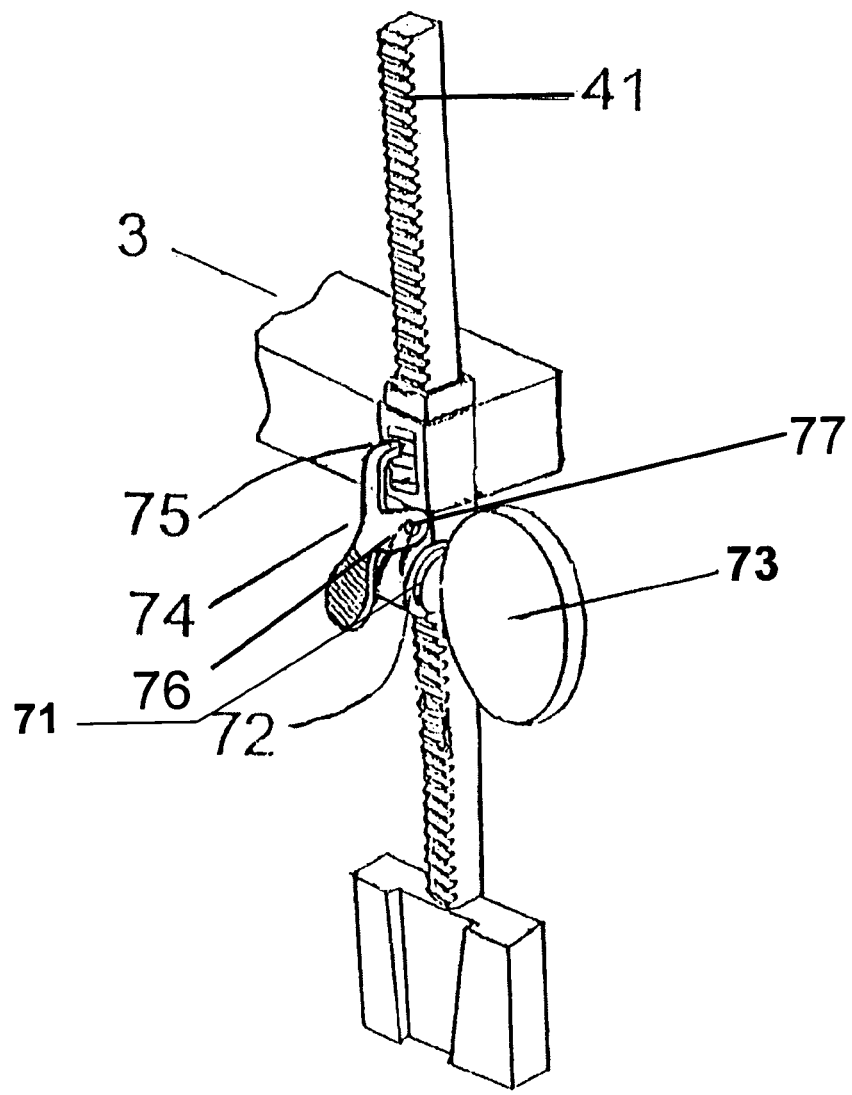
FIG. 7 is a perspective view of another type of lifting mechanism of the rack slider of FIG. 3.

Another type of lifting mechanism 6 is shown in FIG. 7 comprises a pinion 71 having a plurality of teeth (not shown), a pinion housing 72 for positioning the pinion 71 relative to the rack slider 3, a handle 73 to rotate the pinion 71 and a pawl arm 74 having a pawl tooth 75 to secure the rack. The teeth of the pinion 71 matingly engage the teeth 41 of the vertical rack 4. The handle 73 has a bottom end fixedly attached to a portion of the pinion 71 so that rotation of the handle 73 causes the pinion 71 to rotate. This rotation of the pinion 71 correspondingly causes the vertical rack 4 upward. The pawl tooth 75 is of a size to be complementarily received intermediate two adjacent teeth 41 of the vertical rack 4. A spring clip (76) biases the pawl tooth 75 with a bolt (77) to interface with into the teeth 41 of the rack 4 to prevent the free movement of rack. The downward pressure on the pawl arm 74 toward the teeth 41 of the vertical rack 4 is provided by the opposing force of the spring clip (76), which can prevent the tooth 41 to move downwardly.

A preferred aspect of the present invention is that the cross sections of shaft 22 of the horizontal arm 2 and the hole 31 of the rack slider 3 are in circular shape. Other cross sections such as rectangle or other polygon are also applicable. In such a case, since the rack slider 3 is not rotatable on the shaft 22 of horizontal arm 2, the fastening means 5 of rack slider 3 can be a bolt to directly press the arm or even be omitted.

The surgical instrument support structure allows the physician to easily and securely lock vertical post 1 and horizontal arm 2 in place at a desired height above the surgical table. Because the hole 21 of the horizontal arm 2 allow the arm to be slided on the vertical post 1, then the fastening means 5 of the arm 2 can secure the arm 2 on ht evertialc post 1. Following the rack slider 3 can slide on the horizontal arm 2 to the desired position above the abdominal wall. The fastening means of the rack slider 3 can lock it securely on the horizontal arm 2. Furthermore the lifting mechanism 6 can provide the lifting force by turn the handle 61. When the vertical rack 4 is upword, the device coupled with the adaptor 42 will also be raised up to perform a desired physical distension or other manipulation.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

We claim:

1. A lifting apparatus of surgery comprising:
a vertical post;
a horizontal arm;
a rack slider; and
a vertical rack;
said vertical post with one end to be mounted on a surgical table and the other end to be slid on and pivoted by the horizontal arm;
said horizontal arm including a hole, a shaft and a fastening means, wherein the hole of the horizontal arm can slide and pivot on the vertical post, the shaft of the horizontal arm can be slid on by the rack slider and the fastening means of the horizontal arm can secure the horizontal arm on the vertical post;
said rack slider including a hole, and a lifting mechanism, wherein the hole of the rack slider can slide on the shaft of the horizontal arm and the lifting mechanism of the rack slider can engage with the vertical rack, said lifting mechanism comprising a handle, a pivot, two extending pins, a disc, a pinion hole and a rack slot, said handle mounted on one end of the pivot to be rotated by handle, two extending pins on the other end of pivot, which spaced at a proper distance and attached to the disc, to engage with the vertical rack, whereby upon rotating handle to engage extending pins with the vertical rack to form a rack and pinion system; and said vertical rack including a rack and an adaptor, wherein the rack of the vertical rack can engage with the lifting mechanism of the rack slider and the adaptor of the vertical rack can couple with an instrument;

whereby clamping the vertical post on the surgical table, sliding and securing the horizontal arm on the vertical post to desired position, sliding the rack slider on the horizontal arm to desired position above a patient's abdominal wall, engaging the rack slider with the vertical rack, and raising the vertical rack to provide lifting by turning the handle of the lifting mechanism on the rack slider;

wherein said fastening means comprising:

a holding base capable of sliding or rotating on a rod;
a driving bolt rotatably engageable in the holding base;
a thrusting block rotatably coupled with the driving bolt and reciprocatively held in the holding base; and
a follower block engageable with the thrusting block and reciprocatively moving in the holding base;
said holding base including: a rod hole longitudinally formed in the holding base to be slidably engageable with the rod about a longitudinal axis (X); a first block hole transversely formed in the holding base about a first latitudinal axis (Y) projectively perpendicular to the longitudinal axis (X); a screw hole formed in the holding base and coaxially communicated with the first block hole about the first latitudinal axis (Y); and a second block hole transversely formed in the holding base about a second latitudinal axis (Z) perpendicular to the first latitudinal axis (Y) to be perpendicularly intersected with the first block hole;
said driving bolt including: a bolt shank portion, a screw portion having male threads formed thereon and formed on a distal end of the shank portion to be engageable with the screw hole formed in the holding base, a handle formed on a proximal end of the shank portion, and a neck portion annularly recessed in the shank portion adjacent to the handle portion;
said thrusting block including: a sleeve member slidably engageable with the first block hole formed in the holding base, a bolt hole longitudinally formed through the sleeve member and rotatably engageable with the shank portion of the driving bolt, a screw rotatably formed in a screw hole transversely formed through the sleeve member and engageable with the neck portion of the driving bolt for rotatably coupling the driving bolt with the thrusting block, a driving slope surface formed on a side surface of the sleeve member and tapered inwardly towards the first latitudinal axis (Y), a first elongate slot formed in the sleeve member parallel to the first latitudinal axis (Y), and a first limiting screw secured in the holding base and slidably engageable with the first elongate slot for preventing an axial rotation of the sleeve member about the first latitudinal axis (Y); and
said follower block engaging in said second block hole in said holding base and including: a follower wedge face formed on a first end portion of the follower block to be tangentially engageable with the driving wedge face of the thrusting block, a recess portion recessed in a second end portion of the follower block opposite to the follower wedge face in order to interfere in a rod surface circumferentially formed on the rod, a second elongate slot formed in the follower block parallel to the second latitudinal axis (Z), and a second limiting screw secured in the holding base and slidably engageable with the second elongate slot for preventing an axial rotation of the follower block about the second latitudinal axis (Z); whereby upon rotation of the driving bolt for driving the thrusting block inwardly in said base, said follower block will be thrusted to interfere in the rod for firmly fastening the rod in the holding base.

2. A fastening means according to claim 1, wherein said recess portion of said follower block is formed as an arcuate shape in order to be well engaged with a cylindrical rod surface of the rod.

3. A fastening means according to claim 1, wherein said recess portion further includes a packing layer formed on the recess portion to increase a frictional contact with the rod surface of the rod for firmly fastening the rod.

4. A fastening means according to claim 1, wherein said driving bolt includes said cylindrical shank portion annularly formed with a neck portion in said shank portion to be rotatably limited by a limiting screw inserted through the holding base.

5. A lifting mechanism according to claim 1, wherein said turning handle to make vertical rack upward to provide lifting force, and said rack and pinion system locked to resist the forces which tend to downward.

6. A lifting mechanism according to claim 1, wherein said the rack slider further comprising a fastening means to secure the rack slider on the horizontal arm.

7. A lifting apparatus of surgery comprising:
a vertical post;
a horizontal arm;
a rack slider; and
a vertical rack;
said vertical post with one end to be mounted on a surgical table and the other end to be slid on and pivoted by the horizontal arm;
said horizontal arm including a hole, a shaft and a fastening means, wherein the hole of the horizontal arm can slide and pivot on the vertical post, the shaft of the horizontal arm can be slid on by the rack slider and the fastening means of the horizontal arm can secure the horizontal arm on the vertical post;
said rack slider including a hole, and a lifting mechanism, wherein the hole of the rack slider can slide on the shaft of the horizontal arm and the lifting mechanism of the rack slider can engage with the vertical rack, said lifting mechanism comprising a handle, a pivot, two extending pins, a disc, a pinion hole and a rack slot, said handle mounted on one end of the pivot to be rotated by handle, two extending pins on the other end of pivot, which spaced at a proper distance and attached to the disc, to engage with the vertical rack, whereby upon rotating handle to engage extending pins with the vertical rack to form a rack and pinion system; and
said vertical rack including a rack and an adaptor, wherein the rack of the vertical rack can engage with the lifting mechanism of the rack slider and the adaptor of the vertical rack can couple with an instrument;
whereby clamping the vertical post on the surgical table, sliding and securing the horizontal arm on the vertical post to desired position, sliding the rack slider on the horizontal arm to desired position above a patient's abdominal wall, engaging the rack slider with the vertical rack, and raising the vertical rack to provide lifting by turning the handle of the lifting mechanism on the rack slider;

wherein said fasten means comprising:
- a holding base;
- a thrusting bolt; and
- a pressing block;

said holding base including: a rod hole, a cam hole and a bolt hole, wherein the rod hole longitudinally formed in the holding base defining a longitudinal axis at a center of the rod hole and slidably or rotatably engageable with the rod, a cam hole transversely formed in the holding base about a latitudinal axis defined at a center of the bolt hole and projectively perpendicular to the longitudinal axis, and a bolt hole formed in the holding base having a diameter smaller than that of the cam hole and coaxially communicated with the cam hole about the latitudinal axis;

said thrusting bolt including: a handle, a cylindrical shank portion and a screw portion, wherein the cylindrical shank portion connected with the handle and rotatably engageable with the cam hole in the holding base, a cam portion formed on an inner end portion of the shank portion having at least a thrusting sloping portion concentrically formed on the cam portion for operatively engaging and propelling the pressing block inwardly for fastening the rod between the holding base and the pressing block, and a screw portion having male threads formed on the screw portion and engaging with the bolt hole formed in the holding base, with the screw portion protruding inwardly from the shank portion to pass through the pressing block to be engaged with the bolt hole in the holding base;

said pressing block including: a central hole, at least a follower sloping portion, a recess portion and a groove, wherein the central hole formed through the pressing block for passing the screw portion of the thrusting bolt through the central hole, the follower sloping portion concentrically formed on an outer end portion of the pressing block to be tangentially engaged with and inwardly propelled by the thrusting sloping portion formed on the thrusting bolt, a recess portion arcuately recessed in an inner end portion of the pressing block opposite to the follower sloping portion and engageable with a cylindrical surface of the rod in order to interfere in and to firmly fasten the rod between the block and the holding base, the groove longitudinally recessed in a side portion of the pressing block and slidably engaging with a guiding screw inserted through the holding base for longitudinally guiding a reciprocal movement of the pressing block in the bolt hole when driven by the thrusting bolt.

8. A fastening means according to claim 7, wherein said pressing block further includes: a socket recessed in an inner central portion of the pressing block to be coaxially aligned with the central hole of the pressing block for retaining a restoring spring in between the socket and a seat portion formed in the holding base for tensioning the pressing block to be resiliently coupled with the thrusting bolt.

9. A lifting mechanism according to claim 7, wherein said the rack slider further comprising a fastening means to secure the rack slider on the horizontal arm.

10. A lifting mechanism according to claim 7, wherein said turning handle to make vertical rack upward to provide lifting force, and said rack and pinion system locked to resist the forces which tend to downward.

* * * * *